United States Patent [19]
Melnicoff et al.

[11] Patent Number: 5,385,822
[45] Date of Patent: Jan. 31, 1995

[54] METHODS FOR DETECTION AND QUANTIFICATION OF CELL SUBSETS WITHIN SUBPOPULATIONS OF A MIXED CELL POPULATION

[75] Inventors: Meryle J. Melnicoff, Cherry Hill, N.J.; Bruce D. Jensen, Schwenksville, Pa.; Katharine A. Muirhead, West Chester, Pa.; Paul K. Horan, Downingtown, Pa.; Martin D. Summers, West Chester, Pa.; William Wong, Chadsford, Pa.

[73] Assignee: Zynaxis, Inc., Malvern, Pa.

[21] Appl. No.: 619,838

[22] Filed: Nov. 29, 1990

Related U.S. Application Data

[63] Continuation-in-part of Ser. No. 345,436, May 1, 1989, Pat. No. 5,256,532, which is a continuation-in-part of Ser. No. 189,192, May 2, 1988, abandoned.

[51] Int. Cl.$^6$ ............................................. C12Q 1/70
[52] U.S. Cl. ................................... 435/5; 435/7.21; 435/7.24; 435/7.25; 435/7.5; 435/7.94; 435/975; 436/526
[58] Field of Search ............... 435/5, 7.21, 7.24, 7.25, 435/7.5, 7.94, 975, 7.2, 7.22, 7.31, 7.32, 7.33, 7.34, 7.35, 7.36, 7.37; 436/501, 503, 504, 518, 519, 526, 531, 532, 540, 547, 548, 71, 172, 800, 829; 424/11, 417, 450, 86, 87; 530/359, 380, 387, 808

[56] References Cited

U.S. PATENT DOCUMENTS

| | | | |
|---|---|---|---|
| 3,970,518 | 7/1976 | Giaever | 435/239 |
| 4,157,323 | 6/1979 | Yen et al. | 522/84 |
| 4,219,411 | 8/1980 | Yen et al. | 209/213 |
| 4,230,685 | 10/1980 | Senyei et al. | 436/526 |

(List continued on next page.)

FOREIGN PATENT DOCUMENTS

| | | | |
|---|---|---|---|
| 22948/88 | 4/1989 | Australia. | |
| 2012934 | 9/1990 | Canada. | |
| 2012939 | 9/1990 | Canada. | |
| 9002334 | 3/1990 | WIPO | 435/7.24 |

OTHER PUBLICATIONS

Streuli et al., *J. Exp. Med.*, vol. 166, pp. 1548–1566, (1987).

Oellerich, *J. Clin. Chem. Clin. Biochem.*, vol. 22, No. 12, pp. 895–904, (1984).

(List continued on next page.)

*Primary Examiner*—Esther M. Kepplinger
*Assistant Examiner*—Susan C. Wolski
*Attorney, Agent, or Firm*—Dann, Dorfman, Herrell and Skillman

[57] ABSTRACT

The presence or quantity of a selected subset of cells, which is part of a subpopulation of a mixed cell population, is determined by a method in which a detectable reporter substance is uniformly incorporated into substantially all cells of the subpopulation containing the subset of interest. The subset of interest is then affinity-separated by incubating a test sample of the mixed cell population containing the labeled subpopulation with a specific binding substance which selectively binds to characteristic determinants of the cell subset of interest. Occurrence of the reporter substance in the separated fraction is then detected, and correlated to a predetermined standard to determine the presence or quantity of the subset of interest within the cell population. According to another aspect of the invention a method is provided for quantitating two or more selected subsets of cells within a subpopulation of a mixed cell population. After labeling, the entire subpopulation is affinity-separated from the mixed cell population, and occurrence of the reporter substance in the separated fraction is detected. Next, subsets of interest within the subpopulation are affinity-separated as described above, and the level of detected reporter substance in each subset is compared to the level detected in the entire subpopulation. According to further aspects of the invention test kits are provided for performing the above-described methods.

70 Claims, 3 Drawing Sheets

U.S. PATENT DOCUMENTS

| | | |
|---|---|---|
| 4,248,965 | 2/1981 | Mochida et al. ............... 435/7.92 |
| 4,284,412 | 8/1981 | Hansen ............................ 436/808 |
| 4,532,203 | 7/1985 | Ullman ........................ 435/519 X |
| 4,582,797 | 4/1986 | Trowbridge .................. 530/388.7 |
| 4,666,595 | 5/1987 | Graham ........................... 210/222 |
| 4,677,067 | 6/1987 | Schwartz et al. ................. 435/177 |
| 4,710,472 | 12/1987 | Saur et al. ........................ 435/287 |
| 4,727,020 | 2/1988 | Recktenwald ....................... 436/6 |
| 4,748,129 | 5/1988 | Chang et al. ..................... 436/519 |
| 4,876,189 | 10/1989 | Schetters et al. ............... 435/7.24 |
| 4,978,625 | 12/1990 | Wagner ............................ 436/518 |
| 5,085,985 | 2/1992 | Maino et al. .................. 435/7.24 |

OTHER PUBLICATIONS

Bruning et al., *J. Immunol. Meth.*, vol. 33, pp. 33–44, (1980).

Calbiochem, Biochemical/Immunochemical Catalog, pp. 232–234, 1989.

Ralph et al., *Embo Journal*, vol. 6, No. 5, pp. 1251–1257, (1987).

Berman, J. et al., J. Immunol. 138: 2100–2103 (1987).

Brinchmann, J., Clin. Exp. Immunol. 71: 182–186 (1988).

Endl. J. et al., J. Immunol. Methods, 102: 77–83 (1987).

Ghazarossian, V. et al., Clin. Chem. 34/9: 1720–25 (1988).

Kamel, R. S. et al., Clin. Chem., 26/9: 1281–1284 (1980).

Kemshead, J. T. et al., Molec. and Cellular Biochemistry, 67: 11–18 (1985).

Kemshead, J. T. et al., Br. J. Cancer, 54: 771–78 (1986).

Landay, A. et al., Clin. Immunol. Immunopath., 52: 48–60 (1989).

Leivestad, T., Tissue Antigens, 28: 46–52 (1986).

Menz, E. T. et al., Am. Biotech. Lab. (1986).

Moscoso, H. et al., Clin. Chem., 34/5: 902–05 (1988).

Mouton, C. et al., Archives of Biochem. Biophysics, 218: 101–08 (1982).

Nargessi, R. D. et al., J. Immunol., 71: 17–24 (1984).

Rattle, S. J., Clin. Chem., 30/9: 1457–1461 (1984).

Butturini et al., Prog. Bone Marrow Transplant, 413–22 (1987).

CELL CALIBRATION CURVE

BIOTIN CALIBRATION CURVE

PURIFIED LYMPHOCYTES

ENRICHED LEUKOCYTES
(INCLUDES LYMPHOCYTES AND MONOCYTES)

METHODS FOR DETECTION AND QUANTIFICATION OF CELL SUBSETS WITHIN SUBPOPULATIONS OF A MIXED CELL POPULATION

This application is a continuation-in-part of U.S. patent application Ser. No. 345,436, filed May 1, 1989, now U.S. Pat. No. 5,256,532 and entitled "Methods, Reagents and Test Kits for Determination of Subpopulations of Biological Entities", which itself is a continuation-in-part of U.S. patent application Ser. No. 189,192, filed May 2, 1988, now abandoned and entitled "Compounds, Compositions and Methods for Binding Bio-Affecting Substances to Surface Membranes".

FIELD OF THE INVENTION

The present invention relates to biological testing and in particular to methods for determining the presence or quantity of selected subsets of a subpopulation of cells, each subset having at least one characteristic determinant, within a, population of cells, and to test kits used in performing such methods. The methods of the invention facilitate screening of complex biological fluids, such as whole blood, containing small fractions of particular cell types of interest, by means of uniformly incorporating a detectable reporter substance in or on the cells of the subpopulation, then separating the selected subset of interest, e.g., via affinity separation, and detecting the reporter substance.

DESCRIPTION OF THE PRIOR ART

Determinations of components of blood or bone marrow, e.g., subpopulations of leukocytes, have become common clinical diagnostic tests due to the general availability of monoclonal antibodies selectively reactive with determinants of the discrete components. These determinations have proven useful for monitoring changes in immunodeficiency diseases, leukemias, lymphomas and transplant patients. See: A. Landay and K. Muirhead, Clin. Immunol. and Immunopath., 52: 48–60 (1989). Immunofluorescence labeling followed by flow cytometric analysis or fluorescence microscopy is the established method for performing such determinations.

Flow cytometry has decided advantages over other cell marker analysis techniques, such as immunofluorescence microscopy, immunocytochemistry, and enzyme immunoassay. One particular advantage of flow cytometry over bulk methods of marker analysis (e.g. fluorimetry or enzyme immunoassay) is the utilization of multiple detectors to simultaneously analyze multiple signals from each cell. For example, U.S. Pat. No. 4,727,020 to Recktenwald describes the use of two fluorescent channels to detect cells in a subpopulation specifically labeled with two different immunofluorescent agents. U.S. Pat. No. 4,284,412 to Hansen, et al. describes the use of fluorescence channels to detect forward and right angle light scatter of cells of different subpopulations in blood. In both cases, at least one parameter is used for gating so that a signal from a cell (e.g. fluorescence from a fluorochrome) is electronically measured only if the cell falls within the gated subpopulation of interest. Such multiparametric measurement is useful for enumerating subsets of interest within a complex population of cells (e.g. whole blood). This method is time consuming, however, since each sample must be analyzed one cell at a time for the parameters of interest.

Clearly, one distinct disadvantage of flow cytometry is that each sample must be run and analyzed individually. This disadvantage is particularly acute in a clinical laboratory which must process multiple patient specimens daily. The ability to simultaneously quantitate cell subpopulations from multiple samples would substantially reduce the throughput time for this operation in the clinical or research laboratory.

One proposed method for analyzing multiple samples is enzyme-linked immunosorbent assay (ELISA). See: J. Endl. et al., J. Immunol. Meth., 102: 77–83 (1987). See also U.S. Pat. No. 4,876,189 to Shetters et al. This assay measures absorbance of multiple samples at one time using a 96-well microplate reader. The reporter system in this assay utilizes an enzyme conjugated to a monoclonal antibody against a specific antigen and cannot distinguish between an antigen on the subset of interest (e.g. CD4 on lymphocytes) and the same antigen on another subset (e.g. CD4 on monocytes). Consequently, this technique is not well-suited to determination of cell subpopulations in whole blood.

Another method for detection of cell surface antigens or antibodies thereto measures agglutination of fluorochrome labeled erythrocytes. V. Ghazarossian et al., Clin. Chem., .34: 1720-25 (1988); see also U.S. Pat. No. 4,748,129. This method has particular application for blood typing or the detection of antibodies to blood group antigens. Fluorochromes are used to label erythrocyte membranes and the presence of the antibodies or antigens is then determined from fluctuations in the fluorescence signal (detected by a fiber optic probe) due to agglutination of the erythrocytes. This system can produce only qualitative or, at best, semi-quantitative results as to the presence or absence of antigens or antibodies of interest. When the assay is employed to measure the presence of antibodies in plasma, erythrocytes in the blood sample are removed by the addition of colloidal magnetite particles and exposure of the sample to a magnetic field.

In diagnostic testing, it is often desirable to sort out and separate for further analysis a cell subpopulation or subset of interest from a mixed cell population. Affinity separation of cells using protein-coated magnetic particles is known. Various methods for sorting biological populations via magnetic affinity separation have been described in the patent literature and elsewhere. See, for example, U.S. Pat. Nos. 3,970,518, 4,710,472, 4,677,067, 4,666,595, 4,230,685, 4,219,411, 4,157,323; see also, E. T. Menz, et al., Am. Biotech. Lab. (1986); J. S. Kemshead et al., Molec. Cell. Biochem., 67: 11–18 (1985); T. Leivestad et al., Tissue Antigens, 28: 46–52 (1986); and J. S. Berman et al., J. Immunol., 138: 2100-03 (1987). In performing such methods, a binding molecule (e.g., monoclonal antibody) is typically conjugated to the magnetic particles, and added to a test sample under conditions causing binding to a characteristic determinant on the analyte of interest, after which the test sample is exposed to a magnetic field. See, for example, the immunomagnetic separation technique described by Leivestad et al., supra. The magnetic particles and analyte affixed thereto can then be separated from the rest of the population.

The use of magnetic affinity separation has been reported in clinical diagnostic immunoassays for soluble analytes which utilize a radioisotope (see, for example, Rattle et al., Clin. Chem., 30: 1457-61 (1984) or fluorescent molecules (see, for example, Moscoso et al., Clin. Chem., 34: 902–05 (1988); R. D. Nargessi et al., J.

Immunol. Meth., 71: 17–24 (1984); and Kamel et al., Clin. Chem. 26: 1281–84 (1980)) as the reporter substance. The use of this technology to separate certain subpopulations of lymphocytes from bone marrow cells prior to transplantation and to eliminate post-transplantation graft vs. host reaction, has also been reported. See A. Butturini et al., Prog. Bone Marrow Transpl. 413–22 (1987). Other reported uses of this technology include the separation of tumor cells (see: Kemshead et al., B. J. Cancer 54: 771–78 (1986)) and the separation of lymphocyte subpopulations for subsequent functional evaluation (Betman et al., supra).

The application of magnetic affinity cell separation to the quantitation of lymphocyte subsets in blood has been reported. See J. Brinchmann, Clin. Exp. Immunol., 71: 182–86 (1988). In this procedure, blood samples were incubated with superparamagnetic polymer microspheres coated with monoclonal antibodies specific for distinct lymphocyte subpopulations. The cells bound to the microspheres were isolated from the rest of the population by applying a magnetic field to the sample. The separated cells were then lysed to detach them from the microspheres, the microspheres and attached cell membranes were magnetically removed, and the resulting cell nuclei were stained and counted manually with a fluorescent microscope and hemocytometer. The number of nuclei counted corresponded to the number of cells in the sample in the subpopulation of interest. While this procedure may be used to enumerate the cells in a subpopulation of interest, manual enumeration of the cell nuclei is very time consuming and susceptible to technical error in sample loading of the hemocytometer and counting. Such a procedure would not be suitable for use in a clinical setting.

A need exists, therefore, for improved methods to determine the presence or quantity of particular subsets and for subpopulations of cells within a mixed cell population such as that which comprises whole blood. The characteristics of such improved methods should include: sensitivity comparable to or greater than methods heretofore available, ability to analyze multiple samples in a relatively brief time, and elimination of the need for expensive equipment and highly skilled personnel to perform the method.

Our copending U.S. patent application Ser. No. 345,436, discloses several methods for determination of subpopulations of analytes within a population including such analytes. The methods, reagents and test kits of that invention facilitate screening of cells, viruses, and the like, by means of coupling a detectable reporter substance to the bio-membrane, preferably by stable association with the lipid component of the bio-membrane, and thereafter separating the analyte of interest, e.g., by specific binding substances affixed to a solid phase, and detecting the reporter substance. The reagents used in the invention of application Ser. No. 345,436, which are more fully described in our co-pending U.S. application Ser. No. 189,192, provide a distinct advantage over the prior art in that they comprise detectable reporter substances which can become stably associated with the lipid component of a bio-membrane. Thus, analytes containing bio-membranes may be labelled with the detectable reporter substance without relying on specific receptor-ligand interactions. Additionally, because the detectable reporter substance is stably associated with the bio-membrane, problems with leakage or other loss of the reporter substance are avoided.

Although the bio-membrane-labeling methods of application Ser. No. 345,436 offer many advantages over previous methods and are widely applicable to detection and sorting of many different types of analytes, they are of limited utility in certain important clinical applications, such as the detection and quantitation of certain cell subpopulations in whole blood. The assay system described in application Ser. No. 345,436 labels all cells in a test sample or separated fraction of a blood sample, then uses selective separation to isolate the analyte of interest (e.g. the subset of helper T lymphocytes). However, a typical blood sample contains red blood cells, white blood cells (granulocytes, monocytes and lymphocytes) and platelets, all of which are labeled by the described method. Therefore, when labeled with a compound of the class described in application Ser. No. 345,436, much of the signal is present in cells other than lymphocytes. The difficulty which results is that a small amount of contamination by non-lymphocytes in the separated fraction can contribute significantly to the background signal. This background can be as great, or greater, than the signal from the specific lymphocyte subset of interest, particularly in a disease such as acquired immunodeficiency syndrome (AIDS), which is characterized by a reduced number of a particular subset of lymphocytes. Hence, while the assay system of application Ser. No. 345,436 provides advantages over flow cytometry methods in certain applications because of its ability to measure samples in a batch mode without the elaborate equipment and technical assistance needed for flow cytometry, its utility in detection and quantification of minor components of a complex biological fluid, such as whole blood, is limited.

Continued efforts to improve the sensitivity and selectivity of our previously-described assay systems, making them applicable for clinical and diagnostic analysis of cell subsets of interest in a relatively complex cell population, have led to the development of the present invention.

SUMMARY OF THE INVENTION

According to one aspect of the invention, the presence or quantity of a selected subset of cells, which is part of a subpopulation of a mixed cell population, is determined by a method in which a detectable reporter substance is uniformly incorporated into substantially all cells of the subpopulation containing the subset of interest. In a preferred embodiment, the detectable reporter substance is incorporated into the subpopulation of cells by coupling to the surfaces of those cells, in such a manner so as not to interfere with the subsequent specific binding reactions of the method. A test sample of the mixed cell population containing the labeled subpopulation is then incubated with a specific binding substance which selectively binds to characteristic determinants of the cell subset of interest, forming a complex of those cells and the specific binding substance. The complexes are then separated from the mixed cell population, so as to form two fractions, and the occurrence of the reporter substance in one of the separated fractions is detected. Ordinarily, the level of detected reporter substance is correlated to a predetermined standard to determine the presence or quantity of the subset of interest within the cell population.

According to another aspect of the invention, a method is provided for determining the presence or quantity of two or more selected subsets of cells within a population of cells containing a subpopulation which includes the several subsets of interest. A detectable reporter substance is uniformly incorporated into substantially all cells of the subpopulation containing the multiple subsets. A first sample of the mixed cell population containing the labeled subpopulation is then incubated with a reagent comprising specific binding substances which bind selectively to characteristic determinants of the subpopulation, forming a complex of the cells of the subpopulation and the specific binding substances. This complex, which includes the entire labeled subpopulation, is then separated from the mixed cell population and the occurrence of the reporter substance in the separated fraction is detected.

Next, a second sample of the mixed cell population containing the labeled subpopulation, of equivalent volume and cell concentration to the first sample, is incubated with a second reagent comprising a specific binding substance which binds to characteristic determinants of a subset of interest within the subpopulation. Following separation of the complex thus formed, the occurrence of the reporter substance in the second separated fraction is detected. The relative proportion of subset cells to cells of the entire subpopulation is determined by comparing the amount of reporter detected in the second complex with the amount detected in the first complex.

In a preferred embodiment, a cell subpopulation may be analyzed for the presence or quantity of several subsets of interest. The level of detected reporter substance in each sample may be correlated to one or more predetermined standards to determine the presence or quantity of the subsets of interest within the cell population. In another embodiment of the invention, the labeled subpopulation is analyzed to determine the proportion of each of the several subsets in the subpopulation by quantitating the amount of reporter substance associated with each complex relative to the amount of reporter substance associated with the entire subpopulation.

According to further aspects of the invention, test kits are provided for performing the above described methods. The test kits may include various components depending on the nature of the cells sought to be determined. Test kits would typically contain the detectable reporter substance for incorporating into the selected subpopulation and specific binding substances for selective interaction with characteristic determinants of cell subsets of interest. The test kits may include other components, such as one or more standards for determining the presence or quantity of the subsets of interest in the test sample, instructions for the preparation of such standard(s), and, optionally, other accessories useful in carrying out the methods of the invention.

The methods of the invention may be used as an adjunct to, and in certain instances as a replacement for, the above noted analytical techniques currently applied in clinical laboratories, whose purpose is to screen for changes in cell frequency, e.g., flow cytometry or fluorescence microscopy. The methods described herein incorporate the speed associated with bulk analysis (e.g. enzyme immunoassay) with the utilization of multiparametric measurement, which previously was limited to flow cytometric analysis. Moreover, the methods of the invention obviate the complex, expensive equipment and highly skilled personnel requirements of such prior art techniques.

The methods of the invention have at least two notable advantages over the prior art. First, the cell subset of interest may be directly quantitated from whole blood in the clinical setting without intermediate steps. Other methods for determining the absolute concentration of cells in a subset of interest utilize two or more different measurements to obtain the value of interest. For example, flow cytometry measures the proportional rather than absolute number of lymphocytes in a subset. To obtain the absolute blood concentration of a subset of interest (e.g., CD4 lymphocytes), the following calculation must be made:

CD4 lymphocytes per liter blood=(% CD4 lymphocytes)×(% lymphocytes in white blood cells)×(#white blood cells per liter blood)

Such an analysis uses three sets of measurements: flow cytometry, white blood cell count, and differential white cell count. Typically, the flow cytometric analysis is performed in a immunology laboratory while the white blood cell and differential counts are performed in a hematology laboratory. These may be different laboratories within the same facility or may be located at different facilities. However, the data from both laboratories must be compiled in order to obtain the results which are reported to the clinician.

For example, the decision of whether to initiate azidothymidine (AZT) therapy in AIDS patients rests on a measurement of the number of CD4 lymphocytes per liter of the patient's blood. If this number falls below $0.500 \times 10^9$ CD4 cells per liter, AZT therapy is recommended. See State-of-the-Art conference on Azidothymidine Therapy for Early HIV Infection, Am. J. Medicine, 89: 335-44 (September 1990). Since flow cytometric analysis involves the calculations described above, any alteration in the fraction of lymphocytes in blood will cause an error in the calculated CD4 lymphocyte concentration. Neutrophils, which typically comprise half or more of the white blood cells, are fragile and may degrade during specimen storage or transport to the clinical laboratory. A decrease in the fraction of neutrophils in the white blood cells would cause a concomitant increase in the measured fraction of lymphocytes, and thus a potentially erroneous measurement of CD4 lymphocytes per liter of blood. Such a result could lead a physician to recommend against AZT therapy when, in fact, the patient should be receiving it.

Secondly, the methods of the invention provide a bulk assay for selectively quantitating subsets of interest in a given biological fluid. In a heterogenous population, such as whole blood, the subset of interest is identified by the combination of selective labeling by the reporter substance and selective immunoaffinity separation. This advantage is lacking in other prior art methods of bulk analysis.

Other advantages of the present invention will be apparent to those skilled in the art upon consideration of the drawings in conjunction with the detailed description of the invention presented below.

BRIEF DESCRIPTION OF THE DRAWINGS

In FIGS. 5 and 6 X-axis represents percent lymphocytes measured by flow cytometry; Y-axis represents percent lymphocytes measured by immunoaffinity separation. Labeled lymphocytes were incubated with magnetic beads comprising CD4 ( ), CD8 (+), CD2 ( ) or CD19 (Δ) monoclonal antibodies.

DETAILED DESCRIPTION OF THE INVENTION

Figure 1:
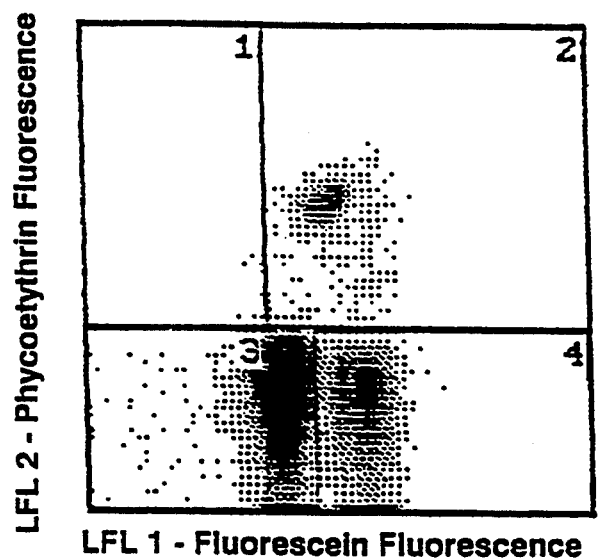
FIG. 1. Flow-cytometric analysis showing immunofluorescence staining pattern of cells labeled with CD45 (clone 2D1, Becton-Dickinson) which labels monocytes and lymphocytes with similar intensity. The x-axis represents the log function of fluorescein fluorescence; the y-axis represents log phycoerythrin fluorescence.

The present invention provides methods for efficiently determining the presence or quantity of selected subsets of a particular subpopulation of cells within a mixed cell population. Analysis is performed on cell suspensions or populations including subpopulations and subsets expressing a characteristic determinant to establish the total number of cells in the subset of interest within a sample cell suspension, or to determine the proportion of a cell subset within a cell subpopulation.

The term "determinant" is used herein in its broad sense to denote an element that identifies or determines the nature of something. When used in reference to the methods of the invention, "determinant" means that portion of the cell involved in and responsible for selective binding to a specific binding substance, the presence of which is required for selective binding to occur. The separation of cells by means of selective interactions between cellular determinants and specific binding substances (for example, a cell surface antigen and its complementary antibody) is referred to herein as "affinity separation".

Cell-associated determinants include, for example, components of the cell membrane, such as membrane-bound proteins or glycoproteins, including cell surface antigens of either host cell or viral origin, histocompatibility antigens, or membrane receptors. One class of specific binding substances used to selectively interact with these determinants are antibodies capable of immunospecifically recognizing same. The term "antibody" as used herein includes monoclonal or polyclonal immunoglobulins and immunoreactive immunoglobulin fragments. Further examples of characteristic determinants and their specific binding substances are: receptor-hormone, receptor-ligand, agonist-antagonist, Fc receptor of IgG-Protein A, avidin-biotin, virus-receptor and lectin-receptor. These are sometimes referred to herein as "specific binding pairs".

The cell subsets of interest may be present in test samples or specimens of varying origin, including biological fluids such as whole blood, serum, plasma, urine, cerebrospinal fluid, amniotic fluid, lavage fluids and tissue extracts.

Such cells of interest include cells of human or animal origin or cultured cells. Of particular interest in diagnostic, therapeutic and research applications are lymphocytes, including B cells, T cells and recognized T cell subsets, such as helper T cells or suppressor/cytotoxic T cells. Different lineages of cells are characterized by expression of characteristic antigens of ligands. For example, B cells from mammalian blood samples express surface ligands distinct from those expressed by T cells from the same sample. Quantitation of one cell subset from the sample may be important in assessing certain pathological conditions. For example, individuals infected with human immunodeficiency virus (HIV) are tested for T helper cells bearing CD4 glycoprotein for purposes of determining the state of disease and monitoring treatment. As discussed earlier, direct measurement of these cells at the time the sample is taken is important for the accurate assessment of the disease condition of the patient. As another example, an abnormally large proportion of a single B cell clone in a patient's blood may be indicative of a leukemic condition. Cells from the same lineage at different stages of differentiation are also distinguishable by expression of characteristic antigens or ligands. for example, as a B lymphocyte develops from a stem cell to a pre-B cell and ultimately to a mature B cell, the cell membrane markers change in a predictable manner as the cell matures. A mature B cell expresses immunoglobulins as ligands on the cell membrane, whereas a pre-B cell expresses only cytoplasmic immunoglobulin heavy chains, which provides the basis for differential reactivity of these cell subsets, permitting subsequent determination. Differential expression of ligands can further provide a basis for assessing pathogenesis such as vital infection. Vitally infected cells may express vital markers which are absent from uninfected cells within the cell population.

In analyzing cell populations for subpopulations or subsets of interest according to the methods of the invention, the cell population, suspended in its natural biological fluid or in a suitable biological or synthetic medium, is initially exposed to a detectable reporter substance capable of becoming uniformly incorporated into substantially all cells of a selected subpopulation.

For purposes of this invention, cells from different specimens in which the reporter is "uniformly incorporated" have a consistent amount of reporter distributed within the subset of interest. These cells may exhibit some variations in the amount of reporter incorporated into each individual cell, but any such variation should be predictable across subsets of interest and across specimens of interest (including pathologic specimens). It should be noted that such variation may not be predictable for all pathologic specimens, for example, specimens of patients with certain T cell leukemia may not be labeled with T cell-selective reporter substances consistently across all specimens. However, variation across specimens would have to be predictable for the pathologic specimens of interest, e.g. AIDS patients. Thus, a reporter which uniformly labeled T lymphocytes might label the subset of helper T cells with a different mean intensity than the subset of suppressor T cells, but if the difference in mean intensity between the subsets is consistent among samples collected from different individuals, the reporter would be suitable for practicing the invention. In a preferred embodiment, a combination of two or more subset specific reporter substances may be utilized to achieve uniform labeling of subsets of interest as further generally described herein and in further detail in Example 2 below.

The expression "reporter substance" is used herein to refer to any substance whose detection or measurement, either directly or indirectly, by physical or chemical means, is indicative of the presence of the cell subpopulation of interest in the test sample. Examples of useful reporter substances include, but are not limited to the following: molecules or ions directly or indirectly detectable based on light absorbance, fluorescence, reflectance, light scatter, phosphorescence, or luminescence properties; molecules or ions detectable by their radioactive properties; and molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules. In a preferred embodiment, the detectable reporter substance comprises the enzyme beta-galactosidase, which is commonly used in an assay wherein a colorless or nonfluorescent substrate is converted to a colored or fluorescent product, which can be spectrally quantitated.

The reporter substance may be uniformly incorporated into cells of a selected subpopulation by coupling to the surfaces of those cells or by entering and becoming internalized within those cells. If coupling to cell surfaces is the means of incorporation, this coupling must not interfere with subsequent binding steps of the method.

Figure 2:
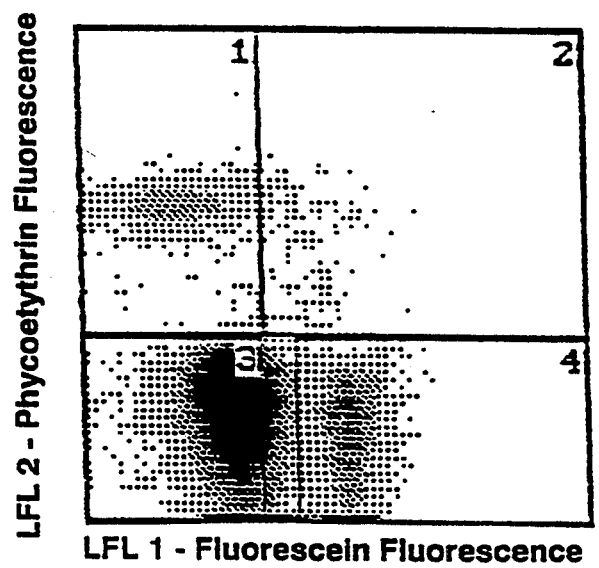
FIG. 2. Flow cytometric analysis showing immunofluorescence staining patterns of cells labeled with CD45 (clone ALB12, AMAC, Inc.) which labels monocytes at much lower intensity than lymphocytes. The x-axis represents the log function of fluorescein fluorescence; the y-axis represents log phycoerythrin fluorescence.

Coupling of the detectable reporter substance to cell surfaces may be achieved by a variety of methods. In a preferred embodiment, the reporter substance is bound to an antibody which itself binds selectively to at least one determinant of the cells of a selected subpopulation, with coupling achieved by an immunological interaction between the cell surface determinant and the antibody. Monoclonal antibodies to particular cell surface determinants are used to great advantage in this embodiment. For example, lymphocytes, which comprise a subpopulation of whole blood, may be uniformly labeled with a reporter substance bound to a monoclonal antibody which is directed against a leukocyte surface antigen. The CD45 antigen is uniformly expressed on all lymphocytes; however, the CD45 antigen is also expressed on monocytes. Therefore, if selective labelling of lymphocytes is desired, it is necessary to select a CD45 monoclonal antibody which binds to significantly more binding sites per cell on lymphocytes than monocytes. Screening for CD45 monoclonal antibodies with the desired properties may be accomplished by methods known in the art, e.g. flow cytometry, as shown in FIGS. 1 and 2 and described herein in Example 1.

In a particularly preferred embodiment, it is desirable to label only T lymphocytes within a sample of whole blood. This may be accomplished as described above, using monoclonal antibodies directed against T cell surface antigens, such as CD2, CD5, CD7 and CD3 antigens, or any combination thereof, to achieve uniform labeling of the T lymphocyte subpopulation.

In the above-described embodiment, direct covalent attachment of the selected reporter substance to the antibody is accomplished by methods known in the art. An alternative strategy is to indirectly link the reporter substance to the antibody by means of an additional specific binding pair of molecules. One such binding pair comprises avidin and biotin. In practice, the antibody may be pre-linked to biotin and the specific binding substance may be pre-linked to avidin. Methods for accomplishing both linkages are reported in the literature and certain biotinylated antibodies and avidin-linked enzymes are commercially available. The coupling of the reporter substance is thus achieved by an immunological interaction between the biotinylated antibody and the cell surface antigen, combined with a biotin-avidin interaction with the avidin-linked reporter substance.

Determination of the presence or quantity of cell subsets according to the methods of the invention is accomplished by the selective interaction between cells of the subset of interest and a specific binding substance. The specific binding substance used in the practice of this invention must exhibit selective recognition for the characteristic cellular determinant. In analyzing a mixed cell population for a subpopulation and/or subset having a characteristic cell surface antigen, for example, the specific binding substance may be the complementary antibody that immunospecifically recognizes the antigen of interest. Based on such selective recognition, the specific binding substance is capable of selective interaction and binding with the subset of interest to form complexes or aggregates which are physically or chemically separate from the test medium and other components therein which are not of interest. In one preferred embodiment, blood specimens containing T lymphocytes and monocytes bearing the surface antigen CD4 are exposed to a specific binding substance comprising a CD4 monoclonal antibody.

Specific binding substances are conveniently affixed to a solid phase or insoluble fluid phase to facilitate separation from the test medium. Techniques for immobilizing antibody on a solid support, e.g., polystyrene, nylon or agarose beads, are well known to those skilled in the art. Suitable techniques include cross-linking, covalent binding or physical absorption. Alternatively, a non-solid phase, primary specific binding substance may be used in conjunction with a second or auxiliary specific binding substance which is capable of interacting selectively with the primary specific binding substance, and which is affixed to a solid phase. Representative primary and auxiliary specific binding substances useful for this purpose are: soluble murine antibody/Protein A affixed to a solid phase; soluble murine antibody/anti-mouse immunoglobulin raised in another species and affixed to a solid phase; biotinylated antibody/avidin affixed to a solid phase.

It should be noted that the use of monoclonal antibodies in both the detectable reporter and the specific binding substance may limit the use of anti-mouse immunoglobulins as an auxiliary binding substance in the above-described method due to cross-reactivity between the anti-mouse immunoglobulin and the two primary mouse antibodies. A similar limitation exists if an auxiliary antibody is used in the reporter system also.

This limitation can be circumvented by employing an auxiliary antibody which is specific for only one subclass of mouse IgG (e.g. IgG1, IgG2a, IgG3) and will therefore react with only one monoclonal antibody in the assay as long as the reporter system and specific binding system utilize antibodies of differing subclasses. For example, the specific binding substance may comprise a CD4 monoclonal antibody of the IgG2b subclass attached to a solid phase via anti-mouse IgG2b. The reporter substance might, therefore, comprise anti-T cell monoclonal antibodies of the IgG1 subclass.

Alternatively, rat monoclonal antibodies may be used in place of mouse monoclonal antibodies in either the reporter substance or the specific binding substance. Thus, the specific binding substance may comprise a CD4 mouse monoclonal antibody attached to a solid phase via an anti-mouse IgG which does not cross-react with rat IgG. The reporter substance would then comprise T cell monoclonal antibodies produced in rats.

In a particularly preferred embodiment of the invention, the specific binding substance is affixed to a magnetic solid phase, which may comprise ferromagnetic, paramagnetic or diamagnetic material, thereby forming complexes or aggregates with the analyte of interest which are magnetically separable from the test medium. Suitable procedures for coupling specific binding substances to a magnetic solid phase, e.g., magnetite particles, are described in the literature. See, for example, E. Menz et al., Am. Biotech. Lab. (1986).

After separation of the cell subset of interest from the test medium, detection of the reporter substance provides a basis for determining the occurrence of interaction between the cells of the subset of interest and the specific binding substance. The reporter substance may be detected in the separated fraction, i.e., in the subset cell/specific binding substance complexes, or in the test medium remaining after separation, which is substantially free of such complexes. The former procedure is preferred.

The level of reporter substance detected in the separated fraction or in the remaining test medium may be correlated to a predetermined standard. Correlation to a standard may be employed whether the determination is qualitative or quantitative. In a qualitative determination, the predetermined standard may be a negative control known to be free of the subset of interest. Detection of the reporter substance in amounts appreciably higher than the background level of the negative control is indicative of the presence of cells of the subset of interest. In a quantitative determination, the level of detected reporter substance is compared to the level detected in e.g., one or more pre-measured quantities of similarly labeled cells, so as to establish the absolute quantity of the cell subset in the test sample.

Quantitative determinations usually involve the preparation of a standard curve, containing increasing known quantities of cells labeled with reporter substance. These known quantities of cells are plotted against the level of reporter substance detected. Based on the standard curve, the quantity of cells comprising a particular subset in a test sample may be derived from the level of reporter substance detected therein.

Because quantitative detection may involve variable parameters, such as temperature-dependent enzymatic activity and instrument-assisted measurements, which may not be consistent from day to day, the cell standard curve must be calibrated against a known quantity of reporter substance. To accomplish this, a standard amount of reporter substance may be affixed to the solid phase used for the affinity separation. In a preferred embodiment, the reporter is affixed to magnetic or paramagnetic material, e.g. beads or particles. Following magnetic separation, the known amount of reporter substance present in the separated fraction can be measured. By comparing the measurements of the cell standard curve with this pre-determined standard quantity of reporter substance, the absolute cells in a sample can be calculated. Furthermore, by attaching the reporter substance to the solid phase in the same way it would be attached in the actual assay, the reporter substance is subject to the same local environment as it would be in the actual assay, thus increasing the accuracy of the calibration.

The reporter substance may be detected in several ways. The presence of reporter substance incorporated with cells in either of the above-mentioned separated portions of the test medium may be determined directly from measurement of the cells and medium using automated methodology. In a preferred embodiment, as described earlier, the detectable reporter substance comprises an enzyme which acts upon a colorless or nonfluorescent substrate to form a spectrally measurable product. For example, beta galactosidase will cleave a nonfluorescent galactose analog (4-methylumbelliferyl-beta-D-galactoside), yielding galactose and a fluorescent product (methylumbelliferone). To overcome problems of steric hindrance, it may be advantageous to remove the detectable reporter substance from the complex before detection. This may be accomplished by chemical cleavage methods known in the art. See, for example, Mouton et al., Arch. Bioch. Biophys., 218: 101–108 (1982).

The foregoing method of the invention may be applied in analyzing a subpopulation of cells present within a mixed cell population to determine the proportional occurrence therein of at least one cell subset of interest. This method may be applied, by way of example and not by way of limitation, to the determination of: lymphocyte, monocyte, and neutrophil subsets of a leukocyte subpopulation in a whole blood cell population; T cells and B cells of a lymphocyte subpopulation in a leukocyte population; or helper T cells and suppressor T cells of a T lymphocyte subpopulation in a total lymphocyte population. In order to determine the proportional occurrence of a subset of cells in this way, it is necessary to determine the relative number of cells in the individual subsets of interest as well as the total number of cells in the subpopulation within the same sample or a sample of equivalent volume and cell concentration.

In carrying out this determination, substantially all of the cells of a population comprising the subpopulation suspected of containing the subsets of interest are uniformly labeled with one or more detectable reporter substances. Affinity separation of the entire subpopulation is accomplished through the use of a first reagent, which includes at least one specific binding substance capable of selectively interacting with a characteristic determinant of the cell subpopulation. This first reagent may be composed of a mixture of specific binding substances, each binding to determinants of the individual subsets of interest within the cell subpopulation, so that substantially all cells of the subpopulation become bound to the first reagent. For example, a number of monoclonal antibodies which interact selectively with the characteristic antigens of a defined number of cell subsets may be included in the first reagent. The first reagent is incubated with a first sample of the population under conditions causing binding of the first reagent to cells of the subpopulation. Next, the complex thus formed is separated from unbound cells in the first sample and the occurrence of reporter substance in the separated complex is detected. This procedure establishes the relative or absolute number of cells within the cell subpopulation of interest.

Thereafter, a second sample of the cell population into which the detectable reporter substance has been incorporated, as described above, having volume and cell concentration equivalent to the first sample, is incubated with a second reagent comprising one or more specific binding substances that selectively binds to a characteristic determinant of a cell subset of interest. The second complex thus formed is separated from unbound cells in the second sample and the occurrence of reporter substance in the second complex is detected.

The proportion of the subset of interest in the cell subpopulation is determined by quantitating the amount of reporter substance associated with the second complex relative to the amount of reporter substance associated with the first complex. In general, the level of detected reporter substance in each subpopulation and/or individual cell subset of interest may be related to a predetermined standard, in the manner previously described, to determine the presence or quantity of the cell subpopulation and/or cell subset of interest in the sample undergoing analysis. This determination of proportional subsets of interest is conveniently performed using reagent affixed to a solid phase, which preferably comprises magnetic material to facilitate separation from the test medium.

If the population contains additional cell subsets of interest, additional reagents may be prepared for affinity separation of each of the additional subsets of interest. The additional reagents are incubated with additional samples of the above-mentioned cell population, each sample once again being of equivalent volume and cell concentration to the first sample. Detection of the reporter substance in the complexes separated from each additional sample provides an indication of the proportional occurrence of the individual subsets of interest within each sample. Thus, the proportional occurrence determination of subsets in the additional samples is carried out in the same manner as the determination of the cell subset of interest in the second sample, described above.

The methods of the invention may be performed using conventional containers, including test tubes, multiwell plates, and the like. Detectors for accurately measuring the level of reporter substance in a test sample, such as a colorimeter, a spectrophotometer, a fluorospectrophotometer, a reflectometer, a liquid scintillation counter or a gamma counter, are commercially available.

According to another aspect of the invention, premeasured quantities of the different reagents, together with the various accessories used in practicing the methods of the invention, including diluents, cleaving agents, solid supports for immobilizing analyte, one or more standards, or instructions for the preparation thereof may be conveniently packaged in a test kit. The reagents included in the test kit may take various forms. The reporter substance may be provided in the form of a solution, together with a suitable diluent for incorporating reporter into cells. The reporter solution may be provided in a container suitable for performing the methods of the invention. Alternatively the reporter substance may be packaged dry, together with separate vials of diluent or solvent for addition to the reporter and/or other reagents in the course of carrying out the methods. The specific binding substance is preferably provided immobilized on a solid support, which may be suspended in a suitable buffer, lyophilized or dried.

As an alternative to surface coupling, another aspect of the invention involves the detectable reporter substance entering and becoming internalized within cells. In a preferred embodiment, the detectable reporter substance comprises a compound capable of entering viable cells, undergoing hydrolysis by intracellular enzymes, the hydrolyzed product being capable of detection by means of fluorescence. The detectable hydrolyzed product remains within the cells during separation of subsets of interest, and can be measured upon extraction from separated complexes. A particularly useful compound for this embodiment is 2'7-bis(2-carboxyethyl)-5-(and-6)carboxyfluorescein, acetoxymethyl ester (BCECFAM), which is hydrolyzed intracellularly to 2',7'-bis (carboxyethyl)-5-(and 6) carboxyfluorescein (BCECF). Other useful compounds include:

1-[2-amino-5-(6-carboxyindol-2-yl)-phenoxy]-2-(2'-amino-5'-methylphenoxy)ethane-N,N,N',N'-tetracetic acid, pentaacetoxymethylester;

3-acetoxy-5'(and 6')-acetoxymethoxycarbonyl-10-dimethylaminospiro[7H-benzo[c]xanthene-7,1'(3'H)-isobenzofuran]-3'-one;

fluorescein diacetate; and 5-(and-6)-carboxyfluorescein diacetate.

Thus, in this aspect of the invention the selected subpopulation comprises all viable cells in a mixed population (e.g. whole blood), which can contain substantial amounts of non-viable cells. It should be noted, however, that a subpopulation of whole blood comprising all viable cells will include several different cell types, including granulocytes, monocytes and lymphocytes. If a particular type of lymphocyte is the cell subset of interest, it is preferable that the surface antigen selected for affinity separation via the specific binding substance appears only on that particular cell subset. Otherwise, additional separation steps may be needed, as described in Example 4 below.

The following examples are provided to describe the invention in further detail. These examples are intended to illustrate specific applications of the methods of the invention and should in no way be construed as limiting the invention. All solvent proportions are given by volume and all temperature in °C., unless otherwise indicated.

EXAMPLES

Example 1

Selective Versus Non-Selective Labeling of Cell Subpopulations with Detectable Reporter Substances To illustrate the advantage of using lymphocyte selective labeling over the methods described in U.S. patent application Ser. No. 345,436, wherein the entire cell population is labeled, the following comparison was made.

A. Labeling of all cells with a reporter substance which is stably associated with the lipid component of biomembranes A blood sample from a healthy individual was stained with 1'-docosanyl-1-propyl-3,3,3',3'-tetramethyl indocarbocyanine iodide (DPTI) by adding 5 ul of DPTI (5 mM in ethanol) to 500 ul of blood. After 5 minutes at room temperature, 5 ml of phosphate buffered saline (PBS) was added with mixing. The cell suspension was centrifuged and the supernatant removed. An aliquot of the stained blood was reserved for analysis of red blood cells, and the remaining blood was treated with hypotonic ammonium chloride (1.5 g/l in tris buffer, pH 7) to lyse red blood cells. The samples were analyzed on a Coulter EPICS TM Profile flow cytometer. Cell subpopulations (e.g. lymphocytes, monocytes, neutrophils, platelets) were identified by their light scatter characteristics (see U.S. Pat. No. 4,284,412 to Hansen et al.), and the mean fluorescence intensity of each subpopulation was determined.

The concentration of each cell type in normal blood and relative fluorescence intensity (i.e. average intensity/cell) of each cell subpopulation, as compared to lymphocytes are shown in Table 1A, columns 1 and 2. From these values, the proportion of the total DPTI signal in each subpopulation was calculated by multiplying the cell concentration by the relative fluorescence intensity of each cell type. Clearly, in whole blood, most of the DPTI signal is associated with red blood cells (column 3).

Using the values calculated above, a theoretical calculation was performed to estimate the relative DPTI signal after a typical immunoaffinity separation, using magnetic beads as described in Example 3 below. Typically, immunoaffinity separation is not absolute; there is almost always some contamination (e.g. 5–10%) of other cell types due to non-specific binding or trapping of the cells. The relative DPTI signal from each cell type after affinity separation of lymphocytes is calculated in columns 4–6. These data show that, when all cells in blood are labeled with reporter substance, such as DPTI, exceptionally selective separation of lymphocytes would be required to measure the signal from lymphocytes without significant signal from contaminating cell types such as red blood cells.

Even if the affinity separation were sufficiently selective to detect a meaningful lymphocyte signal above contaminant signals, the measurement of CD4 lymphocytes in blood would still be complicated by the signal from monocytes, which also bear the CD4 antigen (Table 1B). In a normal individual, the CD4 lymphocytes comprise about 45% of lymphocytes and would produce a signal of 0.45 if total lymphocyte signal is set at 1.00. However, immunoaffinity separation using anti-CD4 would also separate monocytes (relative signal 0.66) for a total signal of 1.11. This problem is more acute when analyzing CD4 lymphocytes from a patient with AIDS, who may possess as few as 5% CD4 lymphocytes; the relative signal from the subset of interest would then be only 0.05 in the presence of a total signal from lymphocytes and monocytes of 0.71.

B. Selective Labeling of Lymphocytes With a Reporter Substance Attached to a Monoclonal Antibody The CD45 antigen is expressed on all leukocytes (lymphocytes, monocytes, and neutrophils), but not on platelets or red blood cells. For analysis of lymphocyte subsets according to the method of the present invention, a CD45 monoclonal antibody (Mab) which binds selectively to lymphocytes is preferred. Selection of such a Mab may be accomplished by flow cytometric analysis.

TABLE 1

WHOLE BLOOD STAINED WITH DPTI (100 μM)

A. DISTRIBUTION OF SIGNAL AMONG SUBPOPULATIONS

| CELL TYPE | BEFORE SEPARATION | | | AFTER SEPARATION | | |
|---|---|---|---|---|---|---|
| | (1) CELLS/ML | (2) RELATIVE INTENSITY | (3) % TOTAL SIGNAL | (4) % CELLS RECOVERED | (5) % TOTAL SIGNAL | (6) RELATIVE SIGNAL |
| RBC | 5.00E+09 | 0.05 | 86.09% | 5.0% | 72.04% | 5.11 |
| GRANULOCYTE | 4.40E+06 | 1.75 | 2.95% | 10.0% | 4.93% | 0.35 |
| MONOCYTE | 5.00E+05 | 2.92 | 0.56% | 10.0% | 0.93% | 0.07 (a) |
| LYMPHOCYTE | 2.20E+06 | 1.00 | 0.84% | 100.0% | 14.09% | 1.00 |
| PLATELET | 2.50E+08 | 0.10 | 9.57% | 5.0% | 8.00% | 0.57 |
| TOTAL | | | 100.0% | | 100.0% | 7.10 |

B. CALCULATION OF SIGNAL AFTER COMPLETE SEPARATION OF CD4+ CELLS

| | RELATIVE SIGNAL FROM | | TOTAL SIGNAL |
|---|---|---|---|
| | LYMPHOCYTES | MONOCYTES | |
| NORMAL BLOOD (45% LYMPHS CD4+) | 0.45 | 0.66 | 1.11 |
| AIDS PATIENT (5% LYMPHS CD4+) | 0.05 | 0.66 | 0.71 |

(a) RELATIVE SIGNAL 0.66 IF ALL MONOCYTES SEPARATED

A blood sample from a healthy individual was collected in EDTA anticoagulant. Two CD45 Mabs were tested; clone 2D1 (Becton-Dickinson) and clone ALB12 (AMAC, Inc.). A sample of blood (100 ul) was incubated with 20 ul of fluorescein conjugated-CD45 and 20 ul of phycoerythrin conjugated-CD14 (AMAC, Inc.), which labels monocytes. The cells were incubated at 4° C. for 30 minutes and then diluted with a ten-fold excess of buffer (phosphate buffered saline with 1% bovine albumin and 0.1% sodium azide). The samples were centrifuged and the supernatants removed. The blood samples were placed on a Coulter Q-Prep TM workstation according to manufacturer's directions. This procedure lyses the red blood cells and fixes the sample for flow cytometric analysis.

The results of the flow cytometric analysis are shown in FIGS. 1 and 2. The histogram of FIG. 1 depicts the relative staining of monocytes and lymphocytes: Quadrant 1 contains cells dimly stained with fluorescein and brightly stained with phycoerythrin; Quadrant 2 contains cells brightly stained with both fluorescein and phycoerythrin; Quadrant 3 contains cells dimly stained with fluorescein and phycoerythrin; Quadrant 4 contains cells brightly stained with fluorescein and dimly stained with phycoerythrin. In this figure, the lymphcoytes comprise the brighter green population (Quadrant 4) and the granulocytes (which include neutrophils) comprise the dimmer green population (Quadrant 3). The monocytes are brightly stained by phycoerythrin, but are also brightly stained with the fluorescein-labeled CD45 and reside in the upper right quadrant (Quadrant 2).

The histogram of FIG. 2 depicts the staining pattern of lymphocytes, monocytes and granulocytes. In this figure, the lymphocytes comprise the brighter green population (Quadrant 4) and the granulocytes comprise the dimmer green population (Quadrant 3). In contrast to the histogram of FIG. 1, the monocytes are brightly stained with phycoerythrin but are only dimly stained with fluorescein labeled-CD45 clone ALB12, and thus, are located in Quadrant 1 rather than Quadrant 2.

Incubation of whole blood with fluorescein labeled CD45, clone 2D1 resulted in bright fluorescein staining of monocytes as well as lymphocytes (FIG. 1). In comparison, CD45 clone ALB12 reacted strongly with lymphocytes, but only weakly with monocytes (FIG. 2). Thus, CD45 clone ALB12 is the clone of preference if selective labeling of lymphocytes relative to monocytes is desired.

The relative fluorescence signal of each cell subpopulation, as compared to lymphocytes, after staining with CD45 clone ALB12, is shown in Table 2A, column 2; the concentration of each of these cell types in a healthy individual is shown in column 1. The calculations in columns 3–6 of Table 2A are as described above for Table 1.

Table 2B shows the signal from various subpopulations when the subset of interest is either all lymphocytes or CD4 lymphocytes. After staining cells with CD45 clone ALB12, the total relative signal in the separated lymphocyte fraction (including non-specific binding of other cell types) is 1.02, of which 1.00 is the signal from the lymphocytes (the subset of interest). When the subset of interest is CD4 lymphocytes in blood from a healthy individual, the relative signal from the subset of interest is 0.45 out of a total singal of 0.46 (assuming no granulocyte contamination). When CD4 lymphocytes from a patient with severe AIDS is the subset of interest, the relative signal from the lymphocytes is 0.05 out of a total signal of 0.06. Thus, selective labeling of lymphocytes significantly reduces the background signal in comparison to the non-selective labeling method described in U.S. patent application Ser. No. 345,436.

Example 2

Use of Monoclonal Antibodies to T-Lymphocytes to Uniformly Label Cells of Interest in a Test Sample One preferred embodiment of the invention enables the direct measurement of the number of cells in a subset of interest in a test sample. Direct quantification of cell number requires that the amount of reporter substance incorporated per cell in the subset of interest be relatively constant among individuals. The following example demonstrates the evaluation of two monoclonal antibodies directed against cell surface antigens for their ability to uniformly label a cell subset of interest.

Two monoclonal antibodies which label T lymphocytes in peripheral blood (CD2 and CD3) were evaluated for variation in epitope density among individuals.

1. Blood samples were collected from 14 donors, 11 healthy individuals and 3 individuals with AIDS, in anticoagulant (heparin or EDTA).
2. 100 ul of blood was incubated with fluorescein conjugated CD2 or CD3 (Becton-Dickinson Immunocytometry Systems) and phycoerythrin conjugated-CD4 (AMAC, Inc.) for 30 minutes at 4° C.
3. 1 ml of buffer (PBS) with 1% bovine albumin and 0.1% sodium azide) was added to each sample with mixing.
4. The samples were centrifuged and the supernatants removed.
5. Tubes containing the labeled blood cells were placed on a Coulter Q-prep TM work station and processed as recommended by the manufacturer. This treatment lyses the red blood cells (RBCs) and fixes the white blood cells (WBCs) for subsequent flow cytometric analysis.
6. Samples were analyzed on a Coulter EPICS Profile TM flow cytometer. Calibration beads (Flow Cytometry Standards Corp.) were included with each day's run.
7. The mean fluorescence intensity of the fluorescein label on the CD4+ cells was determined for each sample. This value was corrected for instrument variation using the calibration beads run on the same day as the sample.

The results of these analyses were:

TABLE 2

WHOLE BLOOD STAINED WITH CD45, CLONE ALB12

A. DISTRIBUTION OF SIGNAL AMONG SUBPOPULATIONS

| | BEFORE SEPARATION | | | AFTER SEPARATION | | |
|---|---|---|---|---|---|---|
| CELL TYPE | (1) CELLS/ ML | (2) RELATIVE INTENSITY | (3) % TOTAL SIGNAL | (4) % CELLS RECOVERED | (5) % TOTAL SIGNAL | (6) RELATIVE SIGNAL |
| RBC | 5.00E+09 | 0.00 | 0.00% | 5.0% | 0.00% | 0.00 |
| GRANULOCYTE | 4.40E+06 | 1.06 | 15.26% | 10.0% | 1.79% | 0.02 |
| MONOCYTE | 5.00E+05 | 0.58 | 0.95% | 10.0% | 0.11% | 0.00 (a) |
| LYMPHOCYTE | 2.20E+06 | 11.64 | 83.79% | 100.0% | 98.10% | 1.00 |
| PLATELET | 2.50E+08 | 0.00 | 0.00% | 5.0% | 0.00% | 0.00 |
| TOTAL | | | 100.0% | | 100.0% | 1.02 |

B. CALCULATION OF SIGNAL AFTER COMPLETE SEPARATION OF CD4+ CELLS

| | RELATIVE SIGNAL FROM | | TOTAL |
|---|---|---|---|
| | LYMPHOCYTES | MONOCYTES | SIGNAL |
| NORMAL BLOOD (45% LYMPHS CD4+) | 0.45 | 0.01 | 0.46 |
| AIDS PATIENT (5% LYMPHS CD4+) | 0.05 | 0.01 | 0.06 |

(a) RELATIVE SIGNAL 0.01 IF ALL MONOCYTES SEPARATED

| EPITOPE (CD) | MEAN FLUORESCENCE INTENSITY OF CD4+LYMPHOCYTES | | |
|---|---|---|---|
| | Mean | Std. Dev. | Coeff. Var. |
| CD2 | 6.9 | 1.15 | 16.6% |
| CD3 | 24.75 | 2.96 | 12.0% |
| CD2+CD3 (calculated) | 31.65 | 2.9 | 9.2% |
| CD2+CD3 (measured) | 33.11 | 2.18 | 6.6% (N = 11) |

These results demonstrate that the biological variation in epitope density among individuals is decreased when two different monoclonal antibodies are used in the reporter system.

Example 3

Assay of Number of CD4 Lymphocytes Per Volume of Blood

Figure 3:
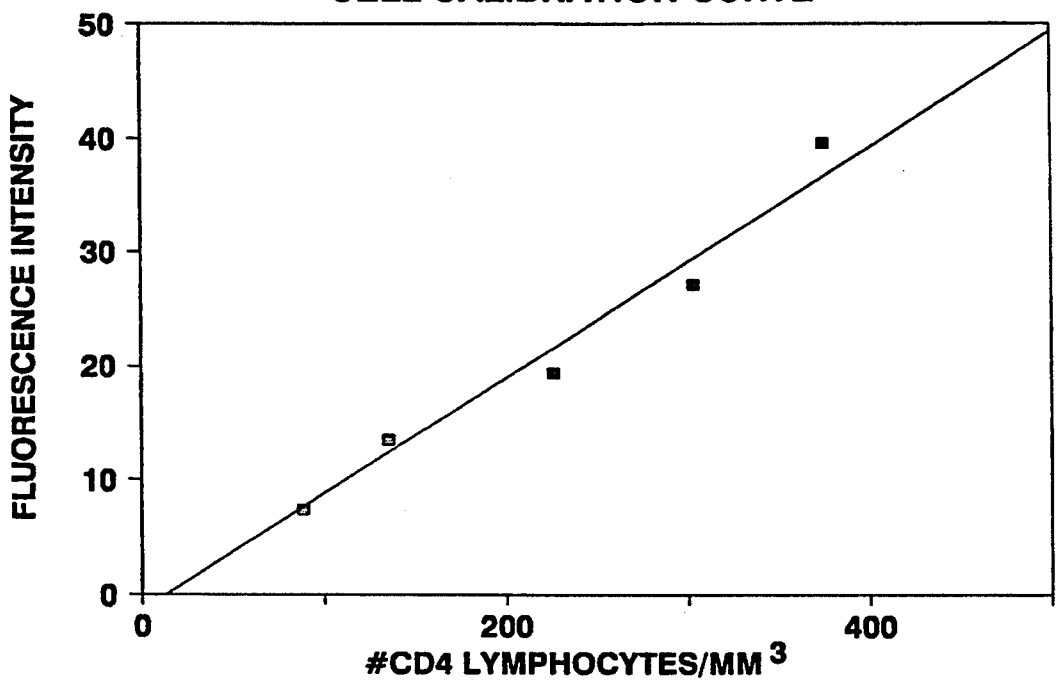
FIG. 3. Cell standard curve. A standard curve of fluorescence intensity versus number of CD4 lymphocytes was generated as described herein. X-axis represents number of CD4 lymphocytes/cubic millimeter; Y-axis represents fluorescence intensity.

A. Preparation of Cell Standard Curve
1. Magnetic beads were prepared:
   a. Monoclonal anti-mouse IgG2a (AMAC, Inc.) was coupled to Tosyl-activated magnetic beads (Dynabeads TM, Dynal, Inc.) according to manufactuer's instructions.
   b. The anti-mouse IgG2a beads were further incubated with either CD4 (Cymbus Bioscience) or negative control monoclonal antibody to form CD4 beads or negative control beads. Both of these monoclonal antibodies were IgG2a subclass.
2. Blood from a healthy donor was collected in heparin anticoagulant.
3. A sample of the blood was incubated with biotin conjugated CD2 (Olympus Immunochemicals; isotype IgG1) for 30 min at 4° C., washed, incubated with beta-galacotsidase conjugated to streptavidin (Southern Biotech) for 30 min at 4° C., and washed again.
4. The blood sample was divided into 2 aliquots. One aliquot was incubated with CD4 beads. The other aliquot was untreated.
5. The blood sample incubated with the magnetic beads were placed on a magnet and the supernatant was removed. This sample was now depleted of CD4 lymphocytes.
6. The CD4 lymphocyte-depleted blood was admixed with the untreated aliquot from step 4 at various ratios ranging from 100% CD4-depleted to 0% CD4-depleted blood. Each admixture, comprising one cell standard, was diluted 1:5 for use.
7. Leukocyte counts were determined on a Coulter counter for each cell standard.
8. Samples of each cell standard were aliquoted for immunofluorescence analysis (for percent CD4 cells) and for use in the standard curve.
9. For the standard curve, 100 ul samples of each cell standard were placed in individual wells of a 96 well plate.
10. 10 ul of magnetic beads, either CD4 or control beads, was added to each well, and plates were incubated for 30 min at 4° C.
11. After incubation, the plate was placed on a magnet for separation of magnetic beads and cells attached to the beads.
12. The supernatant, containing cells not attached to magnetic beads, was removed. The magnetic beads and attached cells were washed 3 times by removing the plate from the magnet, adding 150 ul buffer (PBS with 1% bovine albumin and 0.1% azide) to each well with mixing, placing the plate back on the magnet, and removing the supernatant.
13. The pellet containing the beads and bound cells was incubated with 4-methylumbelliferyl-beta-D-galactoside for 30 minutes at 37° C.
14. The samples were again placed on a magnet and the supernatant (containing methylumbelliferone produced from reaction with beta-galactosidase) was removed to a fresh plate.
15. The fluorescence of the methylumbelliferone was measured with a Fluoroskan TM II microtiter plate reader (Labsystems OY).
16. For immunofluorescence analysis, the sample of each cell standard from step 8 was labeled with fluorescein conjugated-CD4 and phycoerythrin conjugated-CD45. The labeled cells were analyzed by flow cytometry for percent of leukocytes (CD45+) which were CD4+ lymphocytes.
17. The number of CD4 cells in each cell standard was calculated from the leukocyte count and the percent CD4 lymphocytes measured by flow cytometry.
18. A standard curve of fluorescence intensity (measured on the Fluoroskan TM plate reader) versus number of CD4 lymphocytes was generated (see FIG. 3). The slope of this curve was used to determine that one CD4 cell equals 0.066 fluorescence units.

Figure 4:
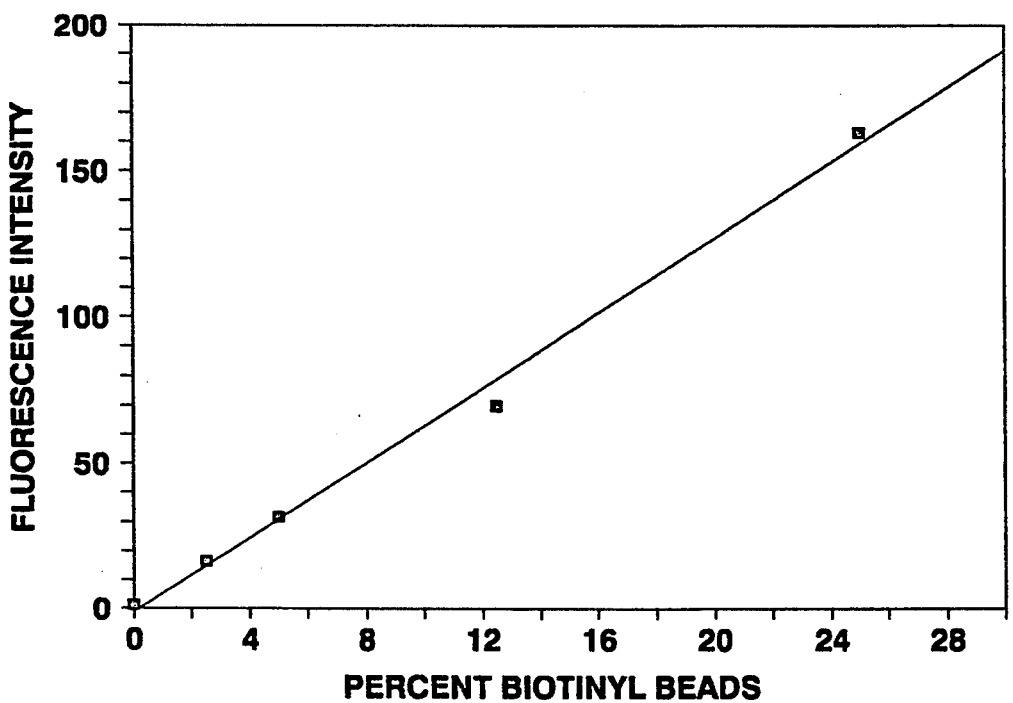
FIG. 4. Biotinylated bead standard curve. A standard curve of fluorescence versus percent biotinylated beads was generated as described herein. X-axis represents percent of biotinylated beads in total bead population; Y-axis represents fluorescence intensity.

B. Preparation of Biotinylated Bead Standard Curve
1. Biotinylated magnetic beads (Advanced Magnetics) were incubated for 30 min with beta-galactosidase conjugated to streptavidin (Southern Biotech), then washed.
2. The beads were then mixed with goat anti-mouse IgG magnetic beads (Advanced Magnetics) in proportions of 0–30% biotinylated beads. Each mixture comprised one bead standard.
3. An aliquot of each bead standard was placed in one well of a 96 well plate, then incubated with 4-methylumbelliferyl-beta-D-galactoside for 30 minutes at 37° C.
4. The plate was placed on a magnet and the supernatant (containing methylumbelliferone produced from reaction with beta-galactosidase) was removed to a fresh plate.
5. The fluorescence of the methylumbelliferone was measured with a Fluoroskan TM II microtiter plate reader (Labsystems OY).
6. A standard curve of fluorescence intensity versus percent biotinylated beads was generated (see FIG. 4). The slope of this curve was used in conjunction with the cell standard curve (FIG. 3) to determine the number of CD4 cell equivalents per percent of biotinylated beads as:

$$\frac{\#CD4 \text{ equiv}}{\% \text{ biotin brad}} = \frac{\text{Fluorescence units}}{\% \text{ biotinylated bead}} \times \frac{1 \ CD4 \text{ cell}}{0.066 \text{ Fluorescence units}}$$

C. Measurement of Number of CD4 Lymphocytes in a Sample of Peripheral Blood
1. Blood was collected in heparin anticoagulant.
2. A sample of the blood was incubated for 30 min with biotin-conjugated CD2 (Olympus Immunochemicals; isotype IgG1), washed, incubated for 30 min with beta-galacotsidase conjugated to streptavidin, and washed again.

3. The blood was diluted 1:5 then 100 ul aliquots were placed in individual wells of a 96 well plate.
4. 10 ul of magnetic beads, either anti-CD4 or control beads, was added to each well.
5. After 30 minutes, the plate was placed on a magnet for separation of magnetic beads and cells attached to the beads. The cells and beads were washed 3 times as described in step 12 of Example 3A.
6. The pellet containing the beads and bound cells was incubated with 4-methylumbelliferyl-beta-D-galactoside for 30 minutes at 37° C.
7. Bead standards, as described above, were added to the same plate and incubated with 4-methylumberlliferyl-beta-D-galactoside for 30 minutes at 37° C.
8. The plate was placed on a magnet and the supernatant (containing methylumbelliferone produced from reaction with beta-galactosidase) was removed to a fresh plate.
9. The fluorescence of the methylumbelliferone in the sample and standard wells was measured with a Fluoroskan TM II microtiter plate reader (Labsystems).
10. The number of CD4 cells per sample was calculated as:

$$\#CD4 = \frac{\text{Fluorescence } CD4\text{-fluorescence control}}{\text{Fluorescence per percent biotin bead}} \times \frac{CD4 \text{ equiv.}}{\% \text{ biotin bead}}$$

11. The percent of leukocytes which were CD4 lymphocytes in each sample was also determined by immunofluorescent staining and flow cytometric analysis, as described in Example 3A. This percent was then multiplied by the leukocyte count to determine the number of CD4 lymphocytes/mm$^3$.
12. Results from 4 healthy donors are:

| | #CD4 lymphs/mm$^3$ | | |
|---|---|---|---|
| Sample | (1) | (2) | (2)/(1) |
| 1 | 1330 | 1550 | 1.2 |
| 2 | 1378 | 1425 | 1.0 |
| 3 | 1243 | 1795 | 1.4 |
| 4 | 2647 | 2400 | 0.9 |

(1) = flow cytometry
(2) = method of invention

Example 4

Comparison of Immunoaffinity Separation with Flow Cytometry Using BCECF AM-Labeled Cells Anticoagulated blood (heparin or EDTA anticoagulant) was collected from 2 healthy donors. Blood samples from each donor were used for preparation of purified lymphocytes and enriched leukocytes.

Purified lymphocytes were prepared as follows: Mononuclear cells were collected by ficoll density gradient centrifugation, then washed once in media (RPMI 1640 [Gibco Laboratories] with 10% fetal bovine serum), resuspended to $1 \times 10^6$ cells per ml, and incubated overnight at 37° C. in a tissue culture flask. Non-adherent cells were recovered, counted, and resuspended to $1 \times 10^6$ per ml in assay buffer (PBS with 1% bovine albumin, 0.05% sodium azide, 40 uM EDTA, and 5 ug/ml indomethacin).

Enriched leukocytes were prepared as follows: Blood was mixed with an equal volume of dextran (2% dextran in PBS) and incubated for 30 minutes at room temperature. The leukocyte enriched supernatant was collected, washed once in assay buffer, and resuspended to $1 \times 10^6$ cells per ml.

Immunomagnetic beads were prepared by incubating goat anti-mouse IgG magnetic beads (Advanced Magnetics) with mouse monoclonal antibodies CD4, CD8, CD19 (from AMAC, Inc.) or CD2 (Olympus Immunochemicals). Goat anti-mouse IgG beads without monoclonal antibodies were used as a negative control.

For the assay, 100 ul of cells were incubated in a 96 well plate with 20 ul beads (bead:cell ratio of 5:1) for 30 minutes at 4° C. with shaking. The magnetic beads and attached cells were separated and washed 4 times with buffer as described in Example 3A.

A 100 uM solution of 2',7'-bis-(2 carboxyethyl)-5-(and-6)carboxyfluorescein, acetoxymethyl ester (BCECF-AM, Molecular Probes) was prepared in assay buffer just prior to use. After the last wash, 180 ul of azide-free assay buffer and 20 ul of the BCECF-AM solution was added to each well. The cells were incubated with BCECF-AM for 30 min at 37° C., then separated on a magnet and the supernatant removed. Triton X-100 (1% in water) was added to each well, 200 ul per well, to lyse the cells and release the fluorescent product, BCECF. Then, 150 ul of the supernatant was transferred to a reading plate and the fluorescence of BCECF was measured on the Fluoroskan TM microtiter plate reader.

The total lymphocyte signal was calculated as the sum of the net signal from CD2 and CD19 (net signal=Mab signal−negative control signal).

For measurement of percent labeled lymphocytes by flow cytometry, a sample of blood from each donor was incubated with fluorescein- or phycoerythrin-conjugated CD4, CD8, CD19, or CD2. The labeled cells were prepared on the Coulter G. Preptin work station as described in Example 2 and then analyzed on a Coulter EPICS TM Profile flow cytometer. Lymphocytes were identified by their light scatter characteristics in the flow cytometer. The percent lymphocytes labeled with each Mab was measured using standard analysis procedures, as described in Landay and Muirhead, supra.

Figure 5:
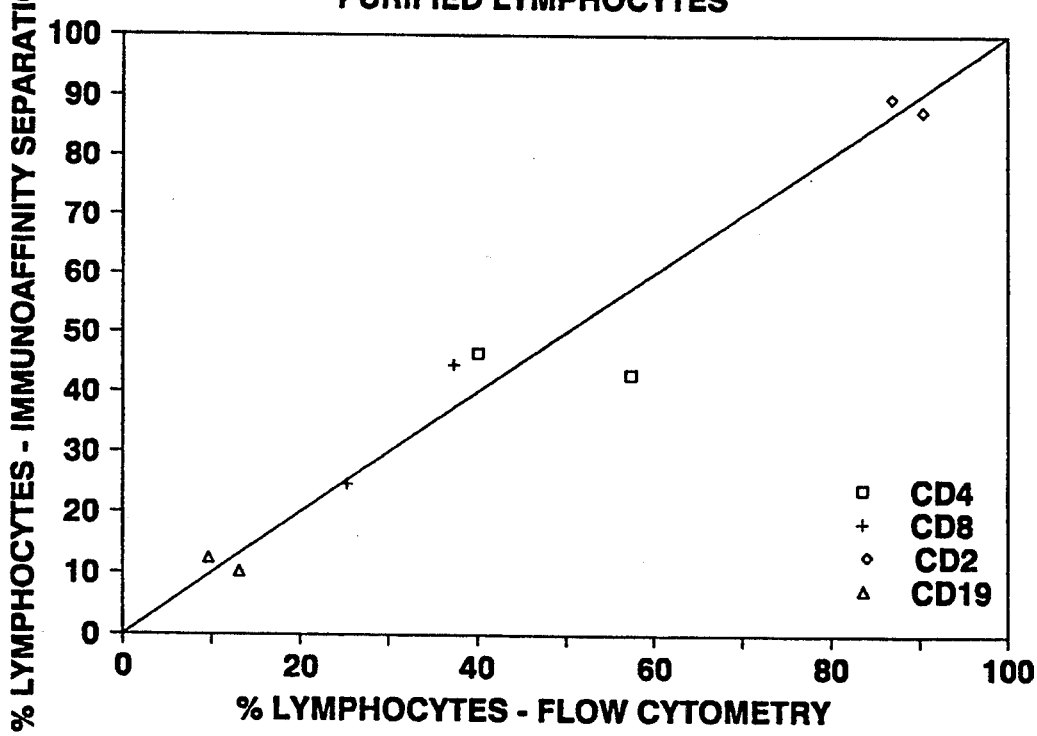
FIG. 5. Correlation of percent lymphocytes measured by immunoaffinity separation versus flow cytometry for analysis of lymphocytes. X-axis represents percent lymphocytes measured by flow cytometry; Y-axis represents percent lymphocytes measured by immunoaffinity separation.
Figure 6:
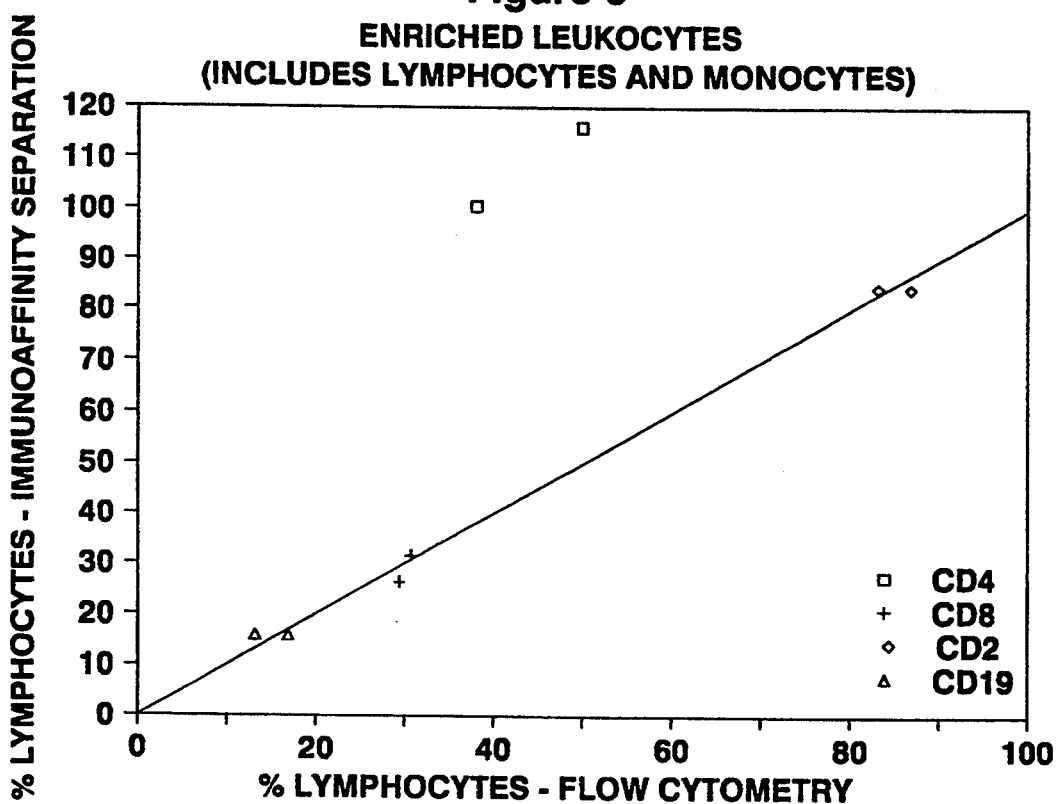
FIG. 6. Correlation of percent lymphocytes measured by immunoaffinity separation versus flow cytometry for analysis of mononuclear cells (lymphocytes and monocytes).

The comparison of the percent lymphocytes identified by each monoclonal antibody using immunoaffinity separation versus flow cytometry, is shown in FIGS. 5 and 6. The ratio of the net signal from each Mab to the total lymphocyte signal was used to calculate the percent lymphocytes measured by immunoaffinity separation in the y axes of FIGS. 5 and 6.

As can be seen from FIG. 5, when monocytes were substantially absent from the sample, results obtained from the method of the invention were comparable to flow cytometry. However, FIG. 6 shows that the quantity of CD4 lymphocytes is overestimated in the assay when the monocytes were not depleted from the sample. This is due to the fact that both monocytes and lymphocytes bear CD4 surface antigens.

The present invention is not limited to the particular embodiments described and exemplified, but is capable of considerable variation and modification without departure from the scope of the appended claims.

What is claimed is:

1. A method for determining the presence or quantity of a selected subset of a subpopulation of cells within a mixed cell population containing said subset, said subpopulation of cells having at least one characteristic determinant and said subset of cells having at least one characteristic determinant, said method comprising:

(i) selectively binding to the cells of said subpopulation a detectable reporter substance, either by a) directly binding a specific binding substance which specifically binds to said at least one characteristic determinant of said subpopulation and which is directly or indirectly conjugated to said detectable reporter substance or b) sequentially binding a first specific binding substance which specifically binds to said at least one characteristic determinant of said subpopulation, and a second specific binding substance which specifically binds to said first specific binding substance and which is directly or indirectly conjugated to said detectable reporter substance, such that a consistent amount of reporter substance is distributed in the subset of interest;

(ii) contacting a test sample of said mixed cell population with a specific binding substance which specifically binds to said at least one characteristic determinant of said selected subset, resulting in the formation of a complex of cells and uncomplexed cells, said complex comprising said selected subset and the specific binding substance that binds to said subset;

(iii) separating said complex from said uncomplexed cells; and (iv) following the completion of Steps (i), (ii), and (iii), detecting the occurrence of said detectable reporter substance in one of said complex or uncomplexed cells, from which the presence or quantity of said selected subset in said mixed cell population is determined.

2. A method according to claim 1, wherein said subpopulation comprises lymphocytes and said subset comprises lymphocytes characterized by selected functions or stages of differentiation.

3. A method according to claim 1, wherein said subpopulation comprises T-lymphocytes and said subset is selected from the group consisting of helper T lymphocytes and suppressor/cytotoxic T lymphocytes.

4. A method according to claim 1, wherein said subpopulation comprises leukocytes and said subset is selected from the group consisting of lymphocytes, monocytes and granulocytes.

5. A method according to claim 1, which includes the step of relating the level of detected reporter substance to a predetermined standard to determine the quantity of said subset of cells in said sample.

6. A method according to claim 1, wherein the level of detected reporter substance is related to a standard containing a predetermined quantity of said reporter substance thereby to determine the number of said subset of cells in said sample.

7. A method according to claim 1, wherein said reporter substance is separated from said complex prior to detecting its presence or quantity.

8. A method according to claim 1, wherein said specific binding substance, which specifically binds to a determinant of said subpopulation, comprises at least one antibody.

9. A method according to claim 8, wherein said reporter substance is attached to one member of a specific binding pair, said antibody is attached to the other member of said specific binding pair, and said selective binding is achieved by the combined effect of immunological binding and binding between the members of said specific binding pair.

10. A method according to claim 9, wherein said specific binding pair comprises avidin and biotin.

11. A method according to claim 10, wherein said biotin is attached to said antibody by a cleavable linkage.

12. A method according to claim 8, wherein said at least one antibody comprises a monoclonal antibody.

13. A method according to claim 12, wherein said monoclonal antibody specifically binds to CD45 antigen.

14. A method according to claim 13 wherein the amount of said monoclonal antibody bound per cell to lymphocytes is at least 5 times greater than the amount bound per cell to monocytes.

15. A method according to claim 12, wherein said at least one antibody comprises a monoclonal antibody that specifically binds T lymphocytes.

16. A method according to claim 15, wherein said at least one antibody comprises a monoclonal antibody which specifically binds to an antigen selected from the group consisting of CD2, CD3, CD5, CD7 or any combination of said monoclonal antibodies.

17. A method according to claim 1, wherein said reporter substance comprises an enzyme.

18. A method according to claim 1, wherein said enzyme is beta-galactosidase.

19. A method according to claim 1, wherein the step of selectively binding said detectable reporter substance to said subpopulation of cells comprises sequentially binding to the surface of the cells, a first antibody which specifically binds to at least one determinant which is common to the cells of said subpopulation, and a second antibody which specifically binds to a determinant of said first antibody, and which is conjugated to said reporter substance.

20. A method according to claim 19, wherein said first antibody comprises a selected isotype and said second antibody specifically binds to a determinant of said isotype.

21. A method according to claim 19, wherein said first antibody comprises immunoglobulin obtained from a selected species and said second antibody specifically binds to a determinant of immunoglobulin from said selected species.

22. A method according to claim 1, wherein said specific binding substance that binds to said subsets is affixed to a solid phase.

23. A method according to claim 22, wherein said solid phase comprises magnetic or paramagnetic material and said complex is separated by magnetic separation.

24. A method according to claim 22, wherein said test sample is contacted in a container with said specific binding substance which specifically binds to said selected subset and said specific binding substance which specifically binds to said selected subset comprises antibody affixed to a surface of said container in contact with said test sample.

25. A method according to claim 1, wherein said specific binding substance to which said selected subset binds comprises an antibody.

26. A method according to claim 25, wherein said antibody comprises a monoclonal antibody.

27. A method according to claim 26, wherein said monoclonal antibody specifically binds the CD4 antigen.

28. A method according to claim 1, wherein the step of contacting said test sample with said specific binding substance which specifically binds to said selected subset additionally includes contacting said test sample with an auxiliary specific binding substance which specifically binds to said specific binding substance which specifically binds to said selected subset, said auxiliary specific binding substance being affixed to a solid phase.

29. A method according to claim 21, wherein said test sample is contacted with a biotinylated antibody as the specific binding substance and with avidin as the auxiliary specific binding substance.

30. A method according to claim 29, wherein said biotin is attached to said antibody by a cleavable linkage.

31. A method according to claim 28, wherein said test sample is contacted with a first antibody as the specific binding substance and with a second antibody as the auxiliary specific binding substance.

32. A method according to claim 31, wherein said first antibody comprises a selected isotype and said second antibody binds selectively to a determinant of said isotype.

33. A method according to claim 31, wherein said first antibody comprises immunoglobulin obtained from a selected species and said second antibody binds selectively to a determinant of said immunoglobulin from said species.

34. A method for analyzing a subpopulation of cells, having at least one characteristic determinant, present within a mixed cell population, said subpopulation of cells including individual subsets of interest, each subset having at least one characteristic determinant, to determine the proportion of at least one selected subset of said subpopulation of cells, comprising:

(i) selectively binding to a portion of cells of said mixed cell population a detectable reporter substance, either by a) directly binding a specific binding substance which specifically binds to a determinant of said portion of cells and which is directly or indirectly conjugated to said detectable reporter substance or b) sequentially binding a first specific binding substance which specifically binds to a determinant of said portion of cells, and a second specific binding substance which specifically binds to said first specific binding substance and which is directly or indirectly conjugated to said detectable reporter substance, whereby said detectable reporter substance uniformly labels substantially all cells of said subpopulation;

(ii) contacting a first sample of said mixed cell population with a first reagent comprising at least one specific binding substance which specifically binds to said at least one characteristic determinant of said cell subpopulation, resulting in the formation of a first complex of cells and uncomplexed cells;

(iii) separating said first complex from said uncomplexed cells;

(iv) following the completion of steps (i), (ii), and (iii), detecting the occurrence of said detectable reporter substance in said first complex;

(v) contacting a second sample of said cell population from step (i), of equivalent volume and cell concentration to said first sample, with a second reagent comprising a specific binding substance which specifically binds to said at least one characteristic determinant of said selected subset of interest included in said subpopulation of cells, resulting in the formation of a second complex of cells and uncomplexed cells;

(vi) separating said second complex from said uncomplexed cells;

(vii) detecting the occurrence of said detectable reporter substance in said second complex; and (viii) determining the proportion of said selected subset of interest in said cell subpopulation by quantitating the amount of said detectable reporter substance associated with said second complex relative to the amount of said detectable reporter substance associated with said first complex.

35. A method according to claim 34, which further comprises:

(ix) contacting one or more additional samples of said mixed cell population from step (i), each sample being of equivalent volume and cell concentration to said first sample, with additional reagents, each said additional reagent comprising a specific binding substance which binds specifically to a characteristic determinant of an additional subset of interest included in said subpopulation of cells, resulting in the formation of additional complexes of cells and uncomplexed cells;

(x) separating each of said additional complexes from said uncomplexed cells;

(xi) detecting the occurrence of said detectable reporter substance in each of said additional complexes; and (xii) determining the proportion of each of said additional subsets in said cell population by quantitating the amount of reporter substance associated with each of said additional complexes relative to the amount of reporter substance associated with said first complex.

36. A method according to claim 35 which includes contacting at least one of said additional samples with an auxiliary specific binding substance which specifically binds to said additional reagent with which said additional sample is contacted, said auxiliary specific binding substance being affixed to a solid phase.

37. A method according to claim 34, wherein said first reagent comprises a mixture of specific binding substances, each said binding substance specifically binding to a characteristic determinant of individual subsets of interest comprising said subpopulation, whereby substantially all cells of said subpopulation are bound to one or another of said binding substances.

38. A method according to claim 34, wherein said subpopulation comprises lymphocytes and said subsets comprise lymphocytes characterized by selected functions or stages of differentiation.

39. A method according to claim 34, wherein said subpopulation comprises T-lymphocytes and said subsets are selected from the group consisting of helper T lymphocytes and suppressor/cytotoxic T lymphocytes.

40. A method according to claim 34, wherein said subpopulation comprises leukocytes and said subsets are selected from the group consisting of lymphocytes, monocytes and granulocytes.

41. A method according to claim 34, wherein said detectable reporter substance is removed from said complex prior to detecting its presence or quantity.

42. A method according to claim 34, wherein said specific binding substance, which specifically binds to a determinant of said portion of cells, comprises at least one antibody.

43. A method according to claim 42, wherein said reporter substance comprises an enzyme.

44. A method according to claim 43, wherein said enzyme is beta-galactosidase.

45. A method according to claim 42, wherein said reporter substance is attached to one member of a specific binding pair, said antibody is attached to the other member of said specific binding pair, and said selective binding is achieved by the combined effect of immunological binding and binding between the members of said specific binding pair.

46. A method according to claim 45, wherein said specific binding pair comprises avidin and biotin.

47. A method according to claim 46, wherein said biotin is attached to said antibody by a cleavable linkage.

48. A method according to claim 42, wherein said at least one antibody comprises a monoclonal antibody.

49. A method according to claim 48, wherein said monoclonal antibody specifically binds to CD45 antigen.

50. A method according to claim 49 wherein the amount of said monoclonal antibody bound per cell to lymphocytes is at least 5 time greater than the amount bound per cell to monocytes.

51. A method according to claim 48, wherein said at least one antibody comprises a monoclonal antibody that specifically binds T lymphocytes.

52. A method according to claim 57, wherein said at least one antibody comprises a monoclonal antibody which specifically binds to an antigen selected from the group consisting of CD2, CD3, CD5, CD7 or any combination of said monoclonal antibodies.

53. A method according to claim 34, wherein the step of selectively binding said detectable reporter substance to said subpopulation of cells comprises sequentially binding to the surface of the cells, a first antibody which specifically binds to at least one determinant which is common to the cells of said portion of cells, and a second antibody which specifically binds to a determinant of said first antibody, and which is conjugated to said reporter substance.

54. A method according to claim 53, wherein said first antibody comprises a selected isotype and said second antibody specifically binds to a determinant of said isotype.

55. A method according to claim 53 wherein said first antibody comprise immunoglobulin obtained from a selected species and said second antibody specifically binds to a determinant of immunoglobulin from said selected species.

56. A method according to claim 34, wherein said specific binding substance of said first reagent and said specific binding substance of said second reagent are each affixed to a solid phase.

57. A method according to claim 56 wherein said second sample is contacted in a sample container with said specific binding substance which specifically binds said selected subset and wherein said specific binding substance which specifically binds said selected subset comprises antibody affixed to a surface of said container in contact with said second sample.

58. A method according to claim 34, wherein said specific binding substance of said first reagent and said specific binding substance of said second reagent are each affixed to magnetic or paramagnetic particles, and said first complex including said subpopulation of interest and said second complex including said selected subset are magnetically separated from said samples.

59. A method according to claim 34, wherein the specific binding substance of each of said first reagent and said second reagent comprises at least one antibody.

60. A method according to claim 34, wherein the specific binding substance of each of said first reagent and said second reagent comprises at least one monoclonal antibody.

61. A method according to claim 60, wherein said monoclonal antibody of said second reagent specifically binds the CD4 antigen.

62. A method according to claim 34 which includes contacting said first sample or said second sample with an auxiliary specific binding substance capable of interacting selectively with said first reagent or said second reagent, respectively, said auxiliary specific binding substance being affixed to a solid phase.

63. A method according to claim 62 wherein said first sample or said second sample is contacted with antibody as the auxiliary specific binding substance.

64. A method according to claim 62 wherein said first reagent or said second reagent comprises antibodies of a selected isotype, and said auxiliary specific binding substance comprises an antibody which binds selectively to a determinant of said isotype.

65. A method according to claim 62 wherein said first reagent or said second reagent comprises immunoglobulin obtained from a selected species, and said auxiliary specific binding substances comprise an antibody which binds selectively to a determinant of said immunoglobulin from said species.

66. A method according to claim 62 wherein said first sample or said second sample is contacted with a biotinylated antibody as the first or second specific binding substance, respectively, and with avidin as the auxiliary specific binding substance.

67. A method according to claim 66 wherein said biotin is attached to said antibody by a cleavable linkage.

68. A test kit for determining the presence or quantity of one or more selected subsets of a subpopulation of cells in a test sample, said subset having at least one characteristic determinant, said test kit comprising:
   (i) a conjugate comprising a detectable reporter substance and a specific binding substance that specifically binds to at least one characteristic determinant of said subpopulation, said conjugate effecting uniform labelling of substantially all cells of said subpopulation by said detectable reporter substance, such that a consistent amount of reporter substance is distributed in the subset of interest; and
   (ii) a reagent comprising at least one specific binding substance affixed to a solid phase, said binding substance being capable of binding to at least one characteristic determinant of one of said subsets.

69. A test kit according to claim 68 which further comprises:
   i) a medium for uniformly labelling cells of said subpopulation with said reporter substance;
   ii) at least one pre-determined standard for determining the presence or quantity of said subsets in said test sample; and
   iii) reagent for detecting said reporter substance.

70. A test kit according to claim 68 wherein said solid phase comprises magnetic or paramagnetic material.

* * * * *